United States Patent [19]

Agharkar et al.

[11] Patent Number: 5,504,102
[45] Date of Patent: Apr. 2, 1996

[54] STABILIZED PHARMACEUTICAL COMPOSITION AND STABILIZING SOLVENT

[75] Inventors: Shreeram N. Agharkar, Fayetteville; Uday S. Gogate, East Syracuse, both of N.Y.

[73] Assignee: Bristol-Myers Squibb Company, New York, N.Y.

[21] Appl. No.: 374,093

[22] Filed: Jan. 18, 1995

Related U.S. Application Data

[62] Division of Ser. No. 128,026, Sep. 29, 1993.

[51] Int. Cl.$^6$ .......................... A01N 43/02; C07D 305/14
[52] U.S. Cl. .................................................. 514/449
[58] Field of Search ................................................ 514/449

[56] References Cited

FOREIGN PATENT DOCUMENTS

51967/93  6/1994  Australia ................. 514/449

*Primary Examiner*—James H. Reamer
*Attorney, Agent, or Firm*—Roylance, Abrams, Berdo & Goodman

[57] ABSTRACT

A stabilized pharmaceutical composition containing paclitaxel, teniposide, camptothecin or other antineoplastic agent susceptible to degradation during storage is produced using a solvent system containing a low carboxylate anion content. The solvent system is a mixture of ethanol and a polyoxyethylated castor oil. The polyoxyethylated castor oil is treated with an acid or contacted with alumina to reduce the carboxylate anion content of the solvent. The low carboxylate anion content of the solvent provides extended shelf life and lower amounts of degradation by-products.

20 Claims, No Drawings

5,504,102

STABILIZED PHARMACEUTICAL COMPOSITION AND STABILIZING SOLVENT

CROSS-REFERENCE TO RELATED APPLICATION

This application is a division of co-pending application Ser. No. 08/128,026, filed Sep. 29, 1993.

FIELD OF THE INVENTION

The present invention is directed to a solvent system suitable for preparing a stabilized injection concentrate containing a pharmaceutical agent. More particularly, the invention is directed to a stabilized injection concentrate using a treated solvent system having a reduced carboxylate anion content and a method for stabilizing a pharmaceutical composition.

BACKGROUND OF THE INVENTION

Pharmaceutical compositions usually require a suitable solvent or carrier system to disperse the active agent to enable the composition to be administered to a patient. The solvent must typically be capable of solubilizing or dispersing a therapeutically effective amount of the active agent to produce an effective injection composition. Moreover, the solvent system must be compatible with the active agent and be non-toxic to the patient.

Numerous pharmaceutical agents are not sufficiently soluble in any one solvent to enable the resulting composition to be effective. To overcome the disadvantages of the limitations of the solvent to solubilize the active agent, mixtures of two or more solvents are sometimes used. These co-solvent systems are suitable for solubilizing many pharmaceutical agents which cannot otherwise be solubilized or dispersed in a carrier system.

One example of a co-solvent system incorporates a mixture of a polar solvent and a non-ionic solvent, such as a mixture of a polyethylene glycol and Cremophor EL. Cremophor EL is a condensation product of castor oil and ethylene oxide sold by BASF. Another suitable co-solvent system for many pharmaceutical agents is a 50:50 mixture of ethanol and Cremophor EL. Although these co-solvent systems can be effective in solubilizing many compounds, they are not without their disadvantages. For example, co-solvents of ethanol and Cremophor are known to result in particulates forming upon dilution with infusion solutions. In addition, fibrous precipitates of unknown composition form in some compositions during storage for extended periods of time. It is generally believed that the precipitates are decomposition byproducts of either components in the solvent or the solubilized agent.

In WO91/02531, published Mar. 7, 1991, Cremophor is disclosed as reversing the multi-drug resistance phenotype of a tumor cell without altering the drug sensitivity of the parent cell line. Cremophor is also disclosed to increase hemopoiesis reconstituting capacity and/or maintain hemopoiesis reconstituting capacity following perturbation of bone marrow to protect a patient during radiation and/or chemotherapy cancer treatments.

Another example of a pharmaceutical composition including a co-solvent system is Taxol which contains paclitaxel in a 50:50 mixture of ethanol and Cremophor EL. Paclitaxel is isolated from the Pacific yew bark and has been used to treat cancer patients. Although the ethanol and Cremophor EL co-solvent system is effective in solubilizing sufficient amounts of the paclitaxel, the resulting composition has been shown to have a limited shelf life. During storage for extended periods of time, the potency or pharmaceutical activity of the composition can decrease as much as 60%.

It has been discovered that commercial grade Cremophor EL with ethanol as a co-solvent, although effective in solubilizing pharmaceutical agents, produces injection compositions that exhibit instability over extended periods of time. In particular, pharmaceutical compositions of Taxol in a co-solvent of 50:50 by volume of dehydrated ethyl alcohol and commercial grade Cremophor EL exhibit a loss of potency of greater than 60% after storage for 12 weeks at 50° C. The loss of potency is attributed to the decomposition of paclitaxel during storage.

Previous efforts to develop a shelf stable composition of some pharmaceutical compositions in various co-solvent systems have not been entirely successful. Thus, there is a continuing need in the art for a co-solvent system capable of being used for preparing stabilized compositions and, in particular, stabilized injection compositions containing a pharmaceutical agent.

SUMMARY OF THE INVENTION

The invention is directed to a solvent system and in particular a co-solvent system suitable for preparing stabilized injection compositions containing at least one pharmaceutical agent. Accordingly, it is a primary object of the invention to provide a method of preparing a solvent and a method of preparing stabilized pharmaceutical compositions including the novel solvent.

The stabilized pharmaceutical composition produced from the solvent system of the invention has been shown to have a shelf life greater than the previous compositions. The co-solvent system of the invention is particularly suitable for use with pharmaceutical compounds that exhibit decomposition which is catalyzed by carboxylate anions. Of particular interest are the antineoplastic agents such as paclitaxel, teniposide, camptothecin and derivatives thereof.

The solvent system of the invention includes a non-ionic solubilizing agent. The solvent system typically includes a solvent and a solubilizing agent. In preferred forms of the invention, the solubilizing agents are polyoxyalkylene modified lipids and alkylene oxides such as polyethylene glycol and derivatives thereof. The solubilizing agent can be a condensation product of an alkylene oxide and a lipid or fatty acid. The preferred solvent system includes a polyoxyethylated castor oil such as that sold under the tradename Cremophor EL. The Cremophor EL is treated to reduce the carboxylate anion content to a sufficiently low concentration to minimize the decomposition of the pharmaceutical agent that is catalyzed by the carboxylate anions. The carboxylate anion content of the Cremophor EL is lowered by either contacting the Cremophor EL with an aluminum oxide bed to separate the carboxylate anions as well as other impurities or by the addition of an acid and particularly a mineral acid such as HCl or $HNO_3$. In further embodiments, the solvent is treated with a reactant to reduce the carboxylate anion or convert the carboxylate anion to a non-reactive form.

The advantages of the invention are also attained by producing a stabilized pharmaceutical composition comprising at least one antineoplastic compound and a solvent capable of dispersing the antineoplastic compound, the solvent comprising a solubilizing amount of a polyoxyethylated castor oil having a carboxylate anion content sufficiently low to substantially prevent carboxylate anion catalyzed degradation of the antineoplastic compound.

Further advantages of the invention are attained by providing a method of stabilizing a pharmaceutical composition containing a pharmaceutical agent selected from the group consisting of paclitaxel and teniposide, and a solvent containing ethanol and a solubilizing amount of at least one solubilizing agent, the method comprising treating the solvent to reduce the carboxylate content to a sufficiently low level to substantially prevent carboxylate anion catalyzed degradation of the pharmaceutical agent.

DETAILED DESCRIPTION OF THE INVENTION

The disadvantages and limitations of the previous injection composition and solvent systems are overcome by the present invention while providing a convenient and efficient method of producing a solvent system and a method of stabilizing pharmaceutical compositions suitable for injection. The present invention is primarily directed to a solvent system suitable for producing a stabilized pharmaceutical composition and to a method of producing and stabilizing a pharmaceutical composition.

It has been surprisingly discovered that paclitaxel reacts with ethanol during storage and that the decomposition of paclitaxel is catalyzed by the carboxylate anions in the solvent. Lowering the carboxylate concentration of the solvent has been found to produce a stabilizing effect in the pharmaceutical composition. The lower carboxylate concentration extends the shelf life of the composition by reducing the rate of decomposition of the pharmaceutical agent and reducing the formation of decomposition byproducts.

The solvent system has a sufficiently low impurity content to provide a stabilizing effect in pharmaceutical compositions. The resulting pharmaceutical composition produced by the method can be used to prepare injection compositions by diluting with a pharmaceutically acceptable carrier or diluent. The composition is sufficiently stable to minimize degradation of the active compound and to reduce the loss of potency during storage. The diluted composition does not exhibit the formation of precipitates so that the pharmaceutically active agent can be stored in a readily usable form.

The pharmaceutical composition in preferred embodiments include at least one pharmaceutical compound having a tendency to degrade during storage where the decomposition reaction is catalyzed by carboxylate anions. The preferred pharmaceutical compounds have antineoplastic activity such as, for example, paclitaxel sold under the tradename Taxol. The various analogs and derivatives of Taxol may also be used.

Taxol is prepared as an injection concentrate containing 6 mg/ml paclitaxel in 50:50 by volume ethanol and polyoxyethylated castor oil. The polyoxyethylated castor oil is sold under the tradename Cremophor EL. Paclitaxel is an active component isolated from the bark of Pacific yew trees. Recently, paclitaxel has been found to be produced in small amounts from a fungus found in the bark of yew trees. Paclitaxel is known to have antineoplastic activity.

Another compound suitable for use in the invention having antineoplastic activity is Teniposide. Teniposide is a semi-synthetic derivative of podophyllotoxin having the chemical name 4'-demethylepiodophyllotoxin 9-(4,6-O-2-thenylidene-β-D-glucopyranoside). Teniposide and the analogs thereof are available from commercial sources and may be prepared by the method disclosed in U.S. Pat. No. 3,524,844.

Another suitable pharmaceutical agent is Camptothecin having the chemical name 4-ethyl-hydroxy-1H-pyrano-[3',4':6,7]indolizino[1,2-b]quinoline-3,14(4H, 12H)dione. Camptothecin is isolated from the stem wood of the Chinese tree and has been shown to exhibit antileukemic and antitumor activity.

The pharmaceutical agents of particular interest are those which exhibit degradation and loss of activity during storage. The solvent system and process of the invention are particularly advantageous for use with pharmaceutical agents that react with or are unstable in the solvent. In particular, the pharmaceutical agents of interest are those having an ester linkage that can be cleaved by an alcohol in the presence of carboxylate anions. Several known pharmaceutical agents when diluted form precipitates after extended periods of time. Although the antineoplastic agents are of particular interest, other pharmaceutical agents which are subject to degradation during storage are also suitable. The pharmaceutical agent alternatively may, for example, be an antifungal or antibacterial.

Paclitaxel is typically produced as a concentrate or solution in a vehicle suitable for injection in the amount of 6 mg/ml. The vehicle is usually a mixture of ethanol and Cremophor EL in the amount of 50:50 by volume. During storage, the activity of the paclitaxel is known to decrease. Paclitaxel has the Formula I, which HPLC shows to degrade into Baccatin III of Formula II and the ethyl ester side chain of Formula III.

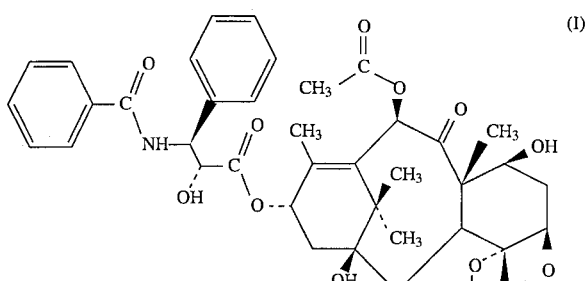

(I)

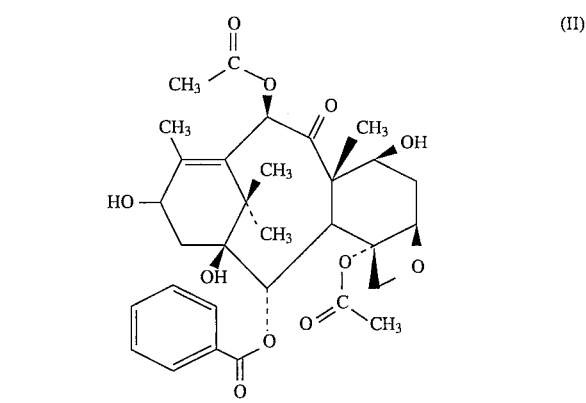

(II)

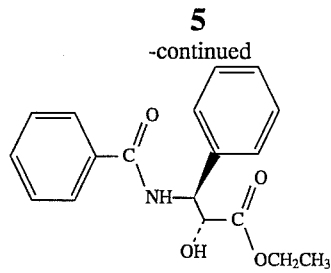

(III)

In preferred embodiments, the solvent is a co-solvent mixture of at least one solvent and a solubilizing agent. The preferred solvents include the alcohols such as dehydrated ethanol and the pharmaceutically acceptable polyols such as polyethyleneglycol. The solubilizing agent in preferred embodiments is a polyoxyethylated castor oil such as that sold under the tradename Cremophor EL by BASF. The co-solvent in preferred embodiments contains about 40% to 60% by volume of the polyoxyethylated castor oil with the balance being an alcohol or polyol. In a particularly preferred embodiment of the invention, the co-solvent comprises about 50:50 by volume of dehydrated ethanol and Cremophor EL.

The co-solvent of the invention preferably includes a non-ionic surfactant as the solubilizing agent with Cremophor EL being the most preferred. Cremophor EL is a condensation product of castor oil and about 20 to 40 moles and preferably 30 to 35 moles of ethylene oxide per mole of castor oil. Cremophor EL may be prepared by the method disclosed in U.S. Pat. No. 3,070,499. Cremophor EL is also known by its common names polyoxyethylene-glycerol triricinoleate and glycerol-polyethyleneglycol ricinoleate. The biological and chemical equivalents or derivatives of Cremophor EL may also be used.

In alternative embodiments, the non-ionic surfactant or solubilizing agent may include other ethylene oxide modified lipids, hydroxylated tallow oils, polysorbate 80, also known as Tween 80, polyethoxylated 12-hydroxy stearic acid, polyoxyethylene sorbitan fatty acid esters, polyethylene glycol esters, polyethylene fatty acid esters, block co-polymers of ethylene oxide and propylene oxide, ethylated fatty alcohol ethers, and octyl-phenoxy polyethoxy ethanol compounds. These non-ionic, solubilizing agents can be produced by methods well known in the art or can be obtained from commercial suppliers. The solubilizer may include other condensation products of alkylene oxides, although the alkylene oxide modified lipids are generally preferred. Examples of suitable solubilizing agents are. PEG 400 and PEG 40 castor oil.

The carboxylate anion content of the solvent can be lowered by a number of methods. In a first embodiment of the invention, the Cremophor EL or other solvent is passed through a standard chromatography column of aluminum oxide. The aluminum oxide adsorbs the carboxylate anions as well as other impurities to reduce the carboxylate anion content of the solvent.

In an alternative embodiment of the invention, the solvent is treated by the addition of an acid in a stabilizing amount to reduce the carboxylate anion content to a sufficiently low level to substantially prevent catalyzed degradation of the pharmaceutical compound. The acid may be added to the solvent before or after admixing with the pharmaceutical compound. Generally, mineral acids such as, for example, HCl, HBr, HF, HI, $H_2SO_4$ and $HNO_3$ are used. Alternatively, organic acids such as acetic may be used. The organic acids are generally less preferred since they can provide a source of carboxylate anions to hinder the stabilizing effect of the acid treatment. The acid is preferably added in amounts to provide $5.6 \times 10^{-6}$ to $8.4 \times 10^{-6}$ grams of $H^+$ per ml of the solvent. Effective stabilization of the composition is obtained by the addition of the acid to provide about $7.0 \times 10^{-6}$ grams of $H^+$ per ml. The acid is added to lower the carboxylate anion content to less than or equal to about $0.6 \times 10^{-6}$ gram equivalents of carboxylate anion per ml of solvent.

Taxol solutions containing $0.6 \times 10^{-6}$ gram equivalents of carboxylate anion have exhibited 94% paclitaxel remaining after storage at 50° C. for 28 days. 1.0 gram equivalents of anions is neutralized by 1.0 gram $H^+$ per equivalent.

The amount of acid added to the solvent will depend on the amount of the non-ionic surfactant in the co-solvent system and the type of the surfactant. The non-ionic surfactants which by their method of preparation inherently contain greater amounts of carboxylate anion impurities will typically require larger amounts of acid to lower the carboxylate anion content.

In further embodiments the solvent may be treated with other reactants which are capable of lowering the carboxylate anion concentration of the solution. For example, insoluble salts of the carboxylates or derivatives of carboxylates may be formed. It is generally preferred to remove the carboxylate anions using a reagent which does not form precipitates in the composition. The addition of a strong mineral acid is generally preferred since the mineral acids and the resulting carboxylic acids are non-toxic and readily solubilized in the solvent. When the carboxylate anions are reacted in a manner which form an insoluble precipitate, the precipitate should be separated from the composition prior to administering the composition to a patient.

The following non-limiting examples are intended to demonstrate the preferred embodiments of the invention. One skilled in the art will readily recognize that numerous embodiments of the invention can be practiced to achieve the stabilizing effect.

EXAMPLE 1

This example analyzes the properties of cleaned and unprocessed Cremophor EL. A first group of samples 1–4 were different batches of processed Cremophor EL and a second group of samples 5–7 were different batches of un-processed commercial grade Cremophor EL. The processed Cremophor EL was prepared by passing 100 Kg of the Cremophor EL through a standard chromatography column containing 19.5 Kg of aluminum oxide sold under the tradename CAMAG. In order to understand the cause of the Taxol instability in unprocessed Cremophor EL, each sample was analyzed by observing the Karl-Fischer moisture, potassium ion content, acid value, and peroxide value. The results of these observations are presented in Table 1.

TABLE 1

| Type of Cremophor EL | Sample No. | KF Moisture % | Potassium level (ppm) | Acid Value | Peroxide Value |
|---|---|---|---|---|---|
| Processed | Sample 1 | 0.2 | <1 | 0.2 | 8 |
|  | Sample 2 | 0.3 | 2 | 0.3 | 8 |
|  | Sample 3 | 0.4 | 2 | 0.2 | 9 |
|  | Sample 4 | 0.8 | 4 | 0.3 | 3 |
| Un-Processed | Sample 5 | 2.7 | 463 | 3.4 | 18 |
|  | Sample 6 | 2.6 | 482 | 1.6 | n.d. |
|  | Sample 7 | 2.6 | n.d. | 1.4 | 15 | n.d = not determined

The data of Table 1 show consistency of moisture content, potassium content, acid value and peroxide value between the batches of processed Cremophor EL used to make samples 1–4. The data further shows consistently higher levels of moisture, potassium content, acid values and peroxide values for the unprocessed Cremophor EL.

EXAMPLE 2

This example was carried out to demonstrate the instability of Taxol and paclitaxel in a co-solvent containing Cremophor EL and to determine the nature of the decomposition products. Specifically, this example was carried out to determine whether high levels of moisture, potassium, acid value and peroxide value of unprocessed Cremophor EL as determined in Example 1 are related to the rate of decomposition and loss of potency of Taxol.

Samples 8–21 were prepared by dissolving 6 mg/ml of paclitaxel in 50:50 v/v mixture of processed Cremophor EL and dehydrated ethanol. The Cremophor EL of samples 8–21 was processed as discussed above in Example 1. Sample 22 was prepared as a control sample from unprocessed Cremophor EL in a 50:50 v/v mixture with paclitaxel in the amount of 6 mg/ml. Each of the samples 8–20 were mixed with the components listed in Tables 2 and 3. Three ml aliquots of the test samples were placed in 6 cc Type I flint glass vials. The vials were stoppered with West 4455/45 Teflon-faced stoppers, sealed and stored for four weeks at 50° C., and then analyzed by HPLC for Taxol concentration. The control parameters of the HPLC are as follows:

| | |
|---|---|
| Column | Jones Cyano RP 5µ, 25 cm × 4.6 mm ID |
| Detector Wavelength | 227 nm |
| Mobile phase | 35% acetonitrile: 65% 20 mM acetate buffer (pH 4) |
| Flow rate | 1.5 mL/min. |
| Diluent | Mobile phase |
| Sample Concentration | 0.05 mg/mL |
| Injection volume | 20 microliters |
| Retention time | Taxol 10.5 mins. |

The pH value for each of the samples was noted following 1:10 dilution with water. Peroxide value (EP method), acid value (USP method), moisture content and potassium levels were determined as shown in Tables 2 and 3.

TABLE 2

| Sample No. | Component Added | % KF Moisture | Initial pH[a] | Following storage for 28 days at 50° C. % taxol remaining | pH[a] |
|---|---|---|---|---|---|
| Sample 8[b] | 4% $H_2O_2$ solution | 5.5 | 4.6 | 94.9 | 3.6 |
| Sample 9[c] | 10% $H_2O_2$ solution | 9.6 | 4.6 | 96.8 | 3.5 |
| Sample 10[d] | 4% water | 5.8 | 5.0 | 94.5 | 4.2 |
| Sample 11[e] | Acetic acid (1.5 mg/mL) | 2.6 | 3.8 | 94.1 | 4.1 |
| Sample 12[f] | None (Control) | 2.6 | 4.4 | 95.5 | 4.5 |

[a]Following 1:10 dilution with Water for Injection.
[b]Peroxide value = 232.
[c]Peroxide value = 652.
[d]Peroxide value = 14.
[e]Acid value = 1.2.
[f]Acid value = 0.5, Peroxide value = 4.

As shown in Table 2, the stability of Taxol as a solution of a 50:50 mixture of dehydrated ethanol and Cremophor EL is not affected by the addition of hydrogen peroxide, water, or acetic acid, thereby demonstrating that the Taxol instability is not related to peroxide value, moisture content or acid value of the Cremophor EL. Each of samples 8–11 exhibited comparable loss of Taxol potency regardless of the reagent added. In each of samples 8–11, the percent of Taxol remaining reflecting the amount of paclitaxel in the samples ranged from 94.1% to 96.8% compared to 95.5% of the control Sample 12.

TABLE 3

| Sample No. | Component Added | $K^-$ level (ppm) | Initial pH[a] | Following Storage for 28 Days at 50° C. % Taxol Remaining | pH[a] |
|---|---|---|---|---|---|
| Sample 13 | CH.COOK 0.126% w/v | 530 | 5.6 | 19.3 | 5.1 |
| Sample 14 | KCl 0.10% w/v | 551 | 6.0 | 98.8 | 4.7 |
| Sample 15 | NaCl 0.125% w/v | 4 | 6.3 | 96.8 | 4.9 |
| Sample 16 | $CH.COONH_4$ 0.10% w/v | 4 | 5.8 | 63.7 | 4.7 |
| Sample 17 | $CH_3COONa$ 0.104% w/v | 5 | 6.1 | 5.8 | 5.5 |
| Sample 18 | $CH_3CH_2COOK$ 0.144% w/v | 468 | 5.4 | 15.2 | 5.1 |
| Sample 19 | Linolelaidic acid (LA) 0.2% W/V | 5 | 6.4 | 99.5 | 5.4 |
| Sample 20 | K salt of LA 0.228% w/v | 150 | 6.3 | 52.8 | 6.2 |
| Sample 21 | None (Control) | >2 | 4.4 | 95.5 | 4.5 |
| Sample 22 | prepared with unprocessed Cremophor EL | ~240 | 4.6 | 86.5 | 4.8 |

[a]Following 1:10 dilution with Water for Injection.

Sample 13 of Table 3 containing potassium acetate is shown to be less stable than control Sample 21 which contained no added component. Sample 14 containing potassium chloride is shown to be comparable with the control Sample 21. These data suggest that the stability of the Taxol is not affected by the presence of potassium ions but rather are adversely affected by the anionic form of the carboxylic acids. Sample 13 containing potassium acetate, Sample 16 containing ammonium acetate, Sample 17 containing sodium acetate, Sample 18 containing potassium propionate and Sample 20 containing potassium linolelaidate are all less stable than the control Sample 22. However, the stability of Sample 11 containing acetic acid and Sample 19 containing linolelaidic acid is comparable to control Sample 22 indicating that the carboxylic acids in the non-ionized form do not affect Taxol stability. Sample 22 containing unprocessed Cremophor EL is also shown to be less stable than control Sample 21 containing processed Cremophor EL. HPLC of each of the samples indicated the degradation products to be Baccatin III and the ethyl ester of the paclitaxel side chain.

EXAMPLE 3

This example demonstrates the stabilizing effect of acids added to Taxol samples containing unprocessed Cremophor EL. The samples in this example were prepared from Taxol containing 6 mg/ml paclitaxel in a 50:50 v/v mixture of dehydrated ethanol and unprocessed commercial grade Cremophor EL. As indicated in Table 4, Samples 23–28 were mixed with HCl, Sample 29 was mixed with acetic acid and Sample 30 was mixed with nitric acid. Sample 31 was the control sample containing no added acid. Sample 32 containing acetic acid and control Sample 33 containing no added acid were also prepared from unprocessed Cremophor EL. The samples were separated into 3 ml aliquots and placed into 5 cc Type 1 flint gloss vials and stoppered with Daikyo #713 fluoresin coated closures. The vials were stored at 50° C. for 56 days and analyzed by HPLC for paclitaxel (Taxol) concentration. The HPLC parameters were as follows:

| | |
|---|---|
| Column | Jones Cyano RP 5µ, 25 cm × 4.6 mm ID |
| Detector Wavelength | 227 nm |
| Mobile phase | 35% acetonitrile: 65% 20 mM acetate buffer (pH 4) |
| Flow rate | 1.5 mL/min. |
| Diluent | Mobile phase |
| Sample Concentration | ~0.05 mg/mL |
| Injection volume | 20 microliters |
| Retention time | paclitaxel ~ 10.5 mins. |

The data in Table 4 demonstrate that the stabilizing effect of the acid increased with increasing amounts of the acid. These results are consistent with the premise that the degradation of Taxol is due to the presence of carboxylate anions rather than the acid. The data further demonstrate that the mineral acids such as HCl and $HNO_3$ are better stabilizing agents with greater than 97% of the Taxol remaining after 56 days when the acid is added at levels to provide $5.6 \times 10^{-6}$ to $8.4 \times 10^{-6}$ grams of $H^+$ per ml. The mineral acids showed a greater stabilizing effect than acetic acid even when the acetic acid was added at a higher level of $70 \times 10^{-6}$ grams of $H^+$ per ml. These results are due to the acid strength of the mineral acids compared to organic acids to neutralize the carboxylate anions. In addition, the acetic acid as a source of carboxylate anions can contribute to some paclitaxel degradation. The amount of paclitaxel remaining in samples 26 and 30 being greater than 100% is due to analytical variations in the measurements.

TABLE 4

| TAXOL | Acid added | | Following Storage for 56 Days at 50° C. | |
|---|---|---|---|---|
| Injection Sample No. | (Gms of $H^+$ added per mL) | Initial $pH^c$ | % Paclitaxel Remaining | $pH^c$ |
| Sample 23[a] | HCl ($3.5 \times 10^{-6}$) | 5.1 | 62.8 | 4.5 |
| Sample 24[a] | HCl ($5.6 \times 10^{-6}$) | 3.9 | 98.1 | 3.8 |
| Sample 25[a] | HCl ($6.3 \times 10^{-6}$) | 3.8 | 97.9 | 3.8 |
| Sample 26[a] | HCl ($7.0 \times 10^{-6}$) | 3.8 | 100.9 | 3.6 |
| Sample 27[a] | HCl ($7.7 \times 10^{-6}$) | 3.6 | 99.3 | 3.6 |
| Sample 28[a] | HCl ($8.4 \times 10^{-6}$) | 3.6 | 99.1 | 3.6 |
| Sample 29[a] | $CH_3COOH$ ($7.0 \times 10^{-6}$) | 4.4 | 69.5 | 4.5 |
| Sample 30[a] | $HNO_3$ ($7.0 \times 10^{-6}$) | 3.7 | 100.4 | 3.8 |
| Sample 31[a] | Control (No acid added) | 5.5 | 49.0 | 5.0 |
| Sample 32[b] | $CH_3COOH$ ($70 \times 10^{-6}$) | 3.7 | 87.8 | 3.7 |
| Sample 33[b] | Control (No acid added) | 6.3 | 22.6 | 5.5 |

[a]Unprocessed Cremophor EL, BASF Lot No. 98-2384, was used in these solutions.
[b]Unprocessed Cremophor EL, BASF Lot No. 14-1213, was used in these solutions.
[c]Following 1:10 dilution with water for Injection.

Samples 34A, 34B, 35A, 35B, 36A and 36B as shown in Table 5 were prepared using different lots of Cremophor to show the consistency of the stabilizing effect of mineral acids. Each sample was prepared containing 6 mg/ml paclitaxel in a 50:50 mixture of dehydrated ethanol and unprocessed Cremophor EL. Samples 34A, 35A and 36A were prepared in the manner of Samples 23–28 and to contain HCl in an amount to provide $7.0 \times 10^{-6}$ of $H^+$ per ml. Control Samples 34B, 35B and 36B did not contain added acid. The samples were stored in closed vials for 56 days at 50° C. The amount of paclitaxel remaining was determined by HPLC as shown in Table 5.

TABLE 5

| Cremophor EL Lot No. - unprocessed | Acid added | Initial $pH^a$ | Following Storage 56 Days at 50° C. | |
|---|---|---|---|---|
| | | | % Paclitaxel Remaining | $pH^a$ |
| Sample 34A | HCl | 4.0 | 98.4 | 3.9 |
| Sample 34B | Control[b] | 6.1 | 25.0 | 5.4 |
| Sample 35A | HCl | 3.9 | 97.8 | 4.0 |
| Sample 35B | Control[b] | 6.3 | 22.6 | 5.5 |
| Sample 36A | HCl | 3.8 | 100.9 | 3.6 |
| Sample 36B | Control[b] | 5.5 | 49.0 | 5.0 |

[a]Following 1:10 dilution with Water for Injection.
[b]No acid was added in the control solutions.

The data of Table 5 demonstrate the consistent stabilizing effect of mineral acids with greater than 97% of the paclitaxel remaining after 56 days compared to less than 50% remaining in the control samples.

The data of Examples 2 and 3 demonstrate the stabilizing effect of processing the Cremophor EL by contacting with aluminum oxide or treating with an acid to reduce the carboxylate content of the solvent. It will be appreciated by those skilled in the art that the process of reducing the carboxylate anion level can be used with other solvents and solubilizers. Taxol is disclosed in the preferred embodiment of the invention which has been demonstrated to exhibit increased shelf life from the stabilizing effect of the acids and the reduction in carboxylate anion content. In further embodiments of the invention, other bioactive agents that are sensitive to carboxylate anion degradation may be used.

What is claimed is:

1. A stabilized composition comprising an antineoplastic compound selected from the group consisting of teniposide, paclitaxel, camptothecin and derivatives thereof; and a solvent capable of dispersing or solubilizing said antineoplastic compound comprising polyoxyethylated castor oil and sufficient acid to provide said solvent with a carboxylate anion content less than or equal to $0.6 \times 10^{-6}$ g equivalents of carboxylate anion per ml of solvent.

2. The composition of claim 1 wherein said solvent further comprises an alcohol.

3. The composition of claim 1 wherein said solvent is a mixture of ethyl alcohol, acid and said polyoxyethylated castor oil.

4. The composition of claim 1 wherein said polyoxyethylated castor oil is a condensation product of castor oil and 20–40 moles of ethylene oxide per mole of castor oil.

5. The composition of claim 1 wherein said acid is a mineral acid.

6. The composition of claim 1 wherein said acid is selected from the group consisting of HCl, HBr, HI, HF, $H_2SO_4$, $HNO_3$ and acetic acid.

7. The composition of claim 1 wherein said solvent contains a mineral acid in an amount to provide about $5.6 \times 10^{-6}$ to $8.4 \times 10^{-6}$ g of $H^+$ per ml of solvent.

8. The composition of claim 1 wherein said antineoplastic compound is teniposide.

9. The composition of claim 1 wherein said antineoplastic compound is camptothecin.

10. A method of preparing a stabilized composition comprising preparing a solvent comprising a polyoxyethylated castor oil and sufficient acid to provide said solvent with a carboxylate anion content less than or equal to $0.6 \times 10^{-6}$ g equivalents of carboxylate anion per ml of solvents, and dispersing an antineoplastic compound selected from the group consisting of teniposide, paclitaxel, camptothecin and derivatives thereof in said solvent.

11. The method of claim 10 wherein said solvent further comprises an alcohol.

12. The method of claim 10 wherein said solvent is a mixture of ethyl alcohol, acid and said polyoxyethylated castor oil.

13. The method of claim 10 wherein said polyoxyethylated castor oil is a condensation product of castor oil, and 20–40 moles of ethylene oxide per mole of castor oil.

14. The method of claim 10 wherein said acid is a mineral acid.

15. The method of claim 10 wherein said acid is selected from the group consisting of HCl, HBr, HI, HF, $H_2SO_4$, $HNO_3$ and acetic acid.

16. The method of claim 10 wherein said solvent contains a mineral acid in an amount to provide about $5.6 \times 10^{-6}$ to $8.4 \times 10^{-6}$ g of $H^+$ per ml of solvent.

17. The method of claim 10 wherein said antineoplastic compound is teniposide.

18. The method of claim 10 wherein said antineoplastic compound is camptothecin.

19. A stabilized composition comprising paclitaxel and a solvent capable of dispersing or solubilizing said paclitaxel comprising polyoxyethylated castor oil and sufficient acid to provide said solvent with a carboxylate anion content less than or equal to $0.6 \times 10^{-6}$ g equivalents of carboxylate anion per ml of solvent.

20. A method of preparing a stabilized composition comprising preparing a solvent comprising a polyoxyethylated castor oil and sufficient acid to provide said solvent with a carboxylate anion content less than or equal to $0.6 \times 10^{-6}$ g equivalents of carboxylate anion per ml of solvents, and dispersing paclitaxel in said solvent.

* * * * *